US009533098B2

(12) United States Patent
Stormer-Talleur et al.

(10) Patent No.: US 9,533,098 B2
(45) Date of Patent: Jan. 3, 2017

(54) INJECTION DEVICE FOR THE NEEDLE-FREE INJECTION OF A MEDIUM

(75) Inventors: Bernd Stormer-Talleur, Hohenhameln (DE); Stephan Theuer, Sehnde (DE); Dirk Schulz, Mannheim (DE); Benedikt Lenzner, Hildesheim (DE)

(73) Assignee: PAINLESS TECH GMBH, Hildesheim (DE)

(*) Notice: Subject to any disclaimer, the term of this patent is extended or adjusted under 35 U.S.C. 154(b) by 0 days.

(21) Appl. No.: 12/743,808

(22) PCT Filed: Nov. 18, 2008

(86) PCT No.: PCT/EP2008/065766
§ 371 (c)(1),
(2), (4) Date: Sep. 1, 2010

(87) PCT Pub. No.: WO2009/065835
PCT Pub. Date: May 28, 2009

(65) Prior Publication Data
US 2011/0009815 A1    Jan. 13, 2011

(30) Foreign Application Priority Data

Nov. 19, 2007  (DE) .................. 10 2007 055 405
Feb. 27, 2008  (DE) .................. 10 2008 011 310
Aug. 28, 2008  (DE) .................. 10 2008 044 830

(51) Int. Cl.
*A61M 5/30*    (2006.01)
*A61M 5/20*    (2006.01)
(Continued)

(52) U.S. Cl.
CPC .......... *A61M 5/2033* (2013.01); *A61M 5/2066* (2013.01); *A61M 5/24* (2013.01);
(Continued)

(58) Field of Classification Search
CPC .... A61M 5/2033; A61M 5/2066; A61M 5/24; A61M 5/30; A61M 5/31515; A61M 5/3129; A61M 2005/3142; A61M 2005/2013; A61M 2005/2073; A61M 2005/3104; A61M 5/3007; A61M 5/31575; A61M 5/2053; A61M 5/31501; A61M 5/31505; A61M 2205/27; A61M 2205/276
(Continued)

(56) References Cited

U.S. PATENT DOCUMENTS 2,459,875 A * 1/1949 Folkman ................. A61M 5/20
                                                    604/135
3,140,713 A * 7/1964 Ismach ................... A61M 5/30
                                                    239/288.5
(Continued)

FOREIGN PATENT DOCUMENTS

CH         694 483 A5    2/2005
DE     690 17 356 T2    6/1995
(Continued)

*Primary Examiner* — Bhisma Mehta
*Assistant Examiner* — Jenna Zhang
(74) *Attorney, Agent, or Firm* — Seed IP Law Group LLP

(57) ABSTRACT

The invention relates to an injection device including an injector and an ampoule unit for the needle-free injection of a medium. A needle-free injection device has a first chamber with an interior that opens into a nozzle, and has a second chamber with an interior that is separated from the interior of the first chamber. The interiors of the two chambers are connectable to each other, thus allowing a mixing and/or reaction of the media located in the chambers. In the first chamber, a powdery medium can be accommodated, and in the second chamber, a fluid medium is can be accommodated. The fluid medium can be transported into the first chamber for the mixing/reaction of the two media.

28 Claims, 14 Drawing Sheets

(51) Int. Cl.
  *A61M 5/24* (2006.01)
  *A61M 5/31* (2006.01)
  *A61M 5/315* (2006.01)

(52) U.S. Cl.
  CPC ............ *A61M 5/30* (2013.01); *A61M 5/3129* (2013.01); *A61M 5/31515* (2013.01); *A61M 2005/2013* (2013.01); *A61M 2005/2073* (2013.01); *A61M 2005/3104* (2013.01); *A61M 2005/3142* (2013.01)

(58) Field of Classification Search
  USPC .............................................. 604/68–72, 115
  See application file for complete search history.

(56) References Cited

U.S. PATENT DOCUMENTS

| | | | |
|---|---|---|---|
| 4,124,024 A | 11/1978 | Schwebel et al. | |
| 4,553,962 A | 11/1985 | Brunet | |
| 4,713,060 A | 12/1987 | Riuli | |
| 4,861,335 A * | 8/1989 | Reynolds | A61M 5/2448 604/191 |
| 5,074,843 A * | 12/1991 | Dalto | A61M 5/30 604/134 |
| 5,137,516 A | 8/1992 | Rand et al. | |
| 5,435,076 A | 7/1995 | Hjertman et al. | |
| 5,693,021 A * | 12/1997 | Diaz | A61M 25/0169 604/171 |
| 5,851,198 A | 12/1998 | Castellano et al. | |
| 5,891,086 A * | 4/1999 | Weston | A61M 5/30 604/143 |
| 6,258,068 B1 | 7/2001 | Kirchhofer et al. | |
| 6,319,224 B1 * | 11/2001 | Stout | A61M 5/30 604/140 |
| 7,056,300 B2 | 6/2006 | Alexandre et al. | |
| 7,837,235 B2 | 11/2010 | Geser et al. | |
| 2003/0050596 A1 | 3/2003 | Alexandre et al. | |
| 2004/0254526 A1 * | 12/2004 | Weston | A61M 5/30 604/68 |
| 2005/0013840 A1 * | 1/2005 | Potter | A61M 5/30 424/422 |
| 2005/0154350 A1 | 7/2005 | Willis et al. | |
| 2005/0192530 A1 * | 9/2005 | Castellano | A61M 5/30 604/70 |
| 2006/0224117 A1 | 10/2006 | Hommann et al. | |
| 2009/0157039 A1 | 6/2009 | Lenzner et al. | |

FOREIGN PATENT DOCUMENTS

| | | |
|---|---|---|
| DE | 20105183 U1 | 6/2002 |
| DE | 10137961 A1 | 3/2003 |
| DE | 102 11 473 A1 | 10/2003 |
| DE | 10 2004 001 451 A1 | 8/2005 |
| DE | 69928012 T2 | 7/2006 |
| EP | 0114145 A2 | 1/1984 |
| EP | 0 367 677 A1 | 5/1990 |
| EP | 0 427 457 A2 | 5/1991 |
| EP | 0 595 508 A1 | 5/1994 |
| EP | 1762261 B1 | 4/2008 |
| GB | 2 404 865 A | 2/2005 |
| WO | 96/15821 A1 | 5/1996 |
| WO | 0035520 A1 | 6/2000 |
| WO | 0158512 A1 | 8/2001 |
| WO | 2005/021071 A1 | 3/2005 |
| WO | 2007065542 A1 | 6/2007 |
| WO | 2007065544 A1 | 6/2007 |

* cited by examiner

Key: A  Spring constant
     B  Spring 1 + 2
     C  Spring 1
     D  Path S

Key: A  Progressive spring
     B  Spring constant
     C  Path S

INJECTION DEVICE FOR THE NEEDLE-FREE INJECTION OF A MEDIUM

BACKGROUND

Technical Field

The invention describes an injection device consisting of an injector and an ampoule unit for the needle-free injection of a medium.

Description of the Related Art

The document DE 699 28 012 T2 describes an injection device, DE 101 37 961 A1 relates to an ampoule for an injection device, DE 201 05 183 U1 relates to an ampoule for a needle-free injection device, EP 1 762 261 B1 discloses a device for the administration of an injectable product, and EP 0 114 145 A2 describes a syringe for medical use. WO 2007/065544 and WO 2007/065542 disclose injection devices.

These documents disclose an injection device for the needle-free injection of a medium, with an injector and an ampoule unit, where the ampoule unit has a basic body which is intended to hold the medium for injection. FIG. 1 shows in detail essentially the embodiment according to the prior art.

FIG. 1 shows in cross section an ampoule unit according to WO 2007/065544. The embodiment shows the structural design of the ampoule unit 1. The latter consists of a basic body 4 which is filled with the medium 3, and which is completely enclosed in the longitudinal direction by a sleeve. At the front end, a nozzle 13 (preferably a steel nozzle) is located which is fixed mechanically in a way that provides a seal for the medium to the basic body 4 or the sleeve 5 via a sealing element 15 (preferably made of silicone), with friction and positive lock by means of a nozzle threading 19. At the outlet of the steel nozzle 13, a cap 14 is screwed on, where a cap seal 20 (made of a sterile material) is located again between the inner wall of the cap 14 and the outlet of the steel nozzle 13.

Before the injection, an ampoule unit as represented in FIG. 1 is screwed on, to apply the medium 3 (or inject it under the skin) after the removal of the cap 14 and of the cap seal 20, after the unit is placed on a certain area of the skin.

BRIEF SUMMARY

The problem of the present invention now is to improve the filling of the injection device, particularly to allow a nearly gas-free filling. Another purpose of the invention is to further develop the injection device, in order to make is usable for additional medical or non-medical purposes (for example, cosmetic purposes), and also to make it possible to administer, with the injection device according to the invention, different media which are mixed together only shortly before the injection or only at the time of the injection.

BRIEF DESCRIPTION OF THE SEVERAL VIEWS OF THE DRAWINGS

FIG. 8a is a cross-sectional view of a nozzle.

FIG. 8b is an elevational view of a portion of the nozzle of FIG. 8a.

DETAILED DESCRIPTION

Figure 1:
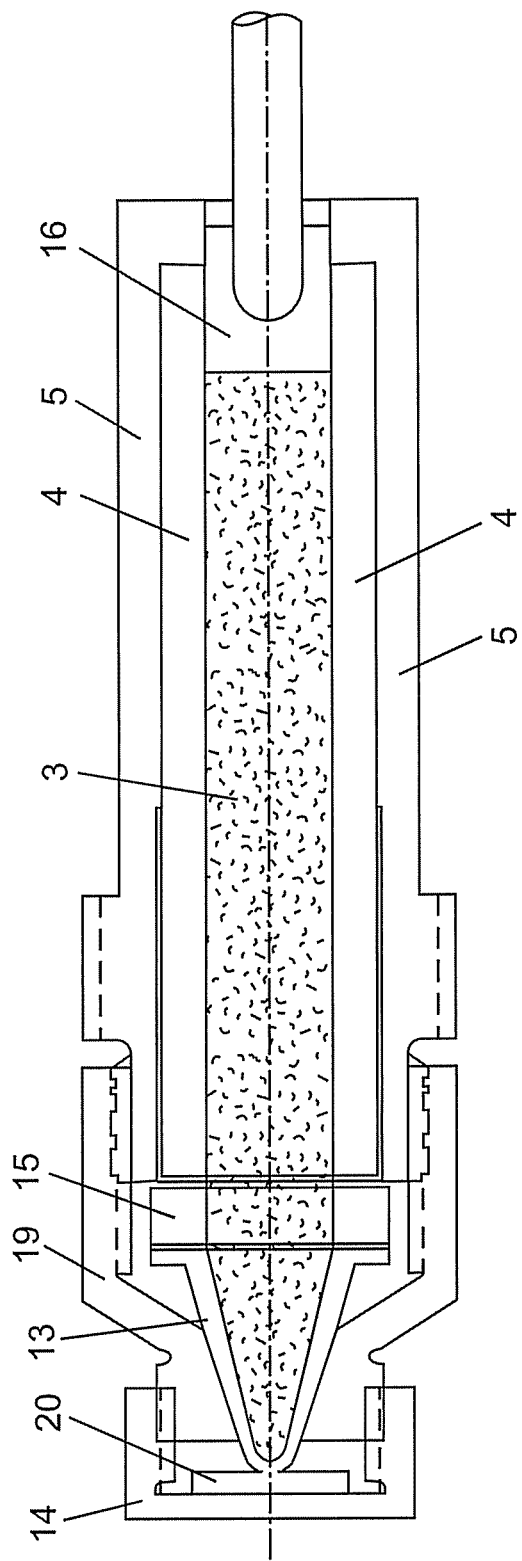
FIG. 1 is a cross-sectional view of a conventional an ampoule unit.
Figure 2A:
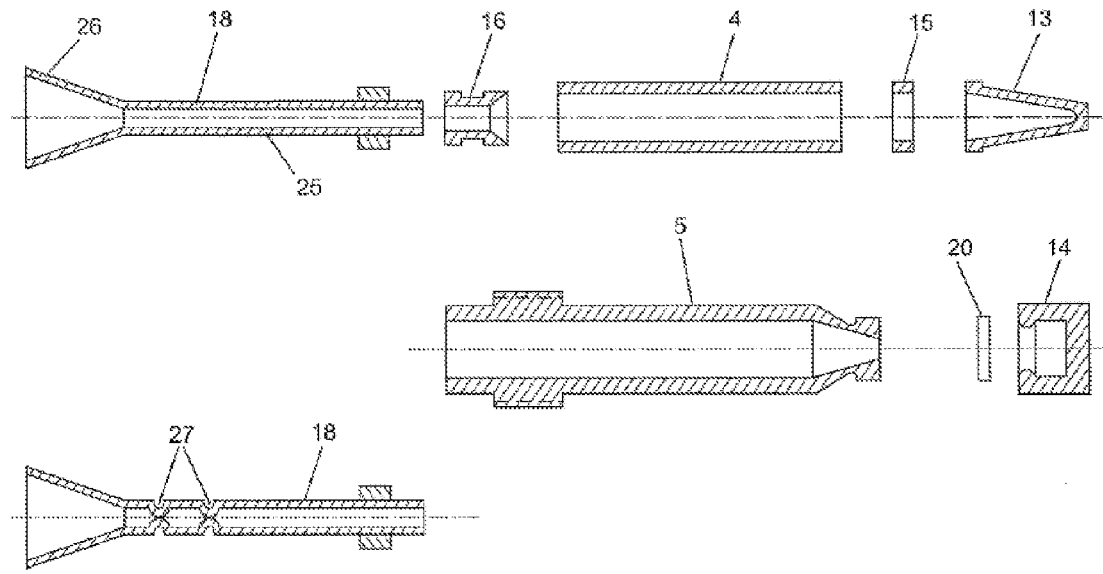
FIG. 2a is an exploded view of an injection device, according to one illustrated embodiment, with a filling neck shown with and without mechanical narrowing.
Figure 2B:
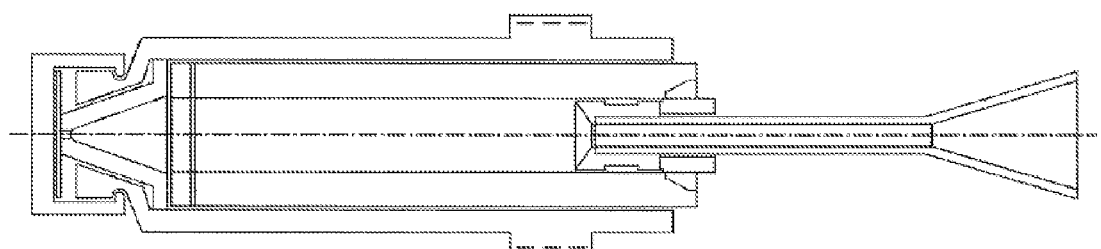
FIG. 2b is a cross-sectional view of an injection device with a filling neck shown without mechanical narrowing.
Figure 2C:
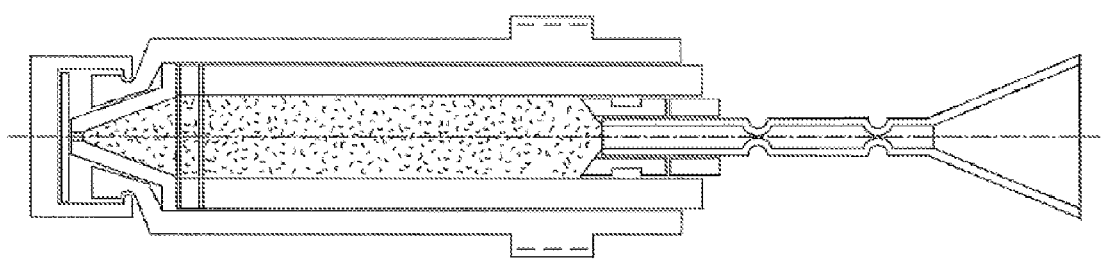
FIG. 2c is a cross-sectional view of an injection device with a filling neck shown with mechanical narrowing.

One design improvement for filing the ampoule unit is shown in FIGS. 2a-2c.

FIG. 2a shows an exploded view of the device according to the invention; FIG. 2b and FIG. 2c show the ampoule unit according to the invention in different embodiments.

Of importance for a nearly gas-free filling is a seal 16 which has a conical cross section as shown in FIG. 2 and which is located in the space between the basic body 4 (made preferably of glass or a similar material, for example, TOPAS) and a filling neck 18. This filling neck 18 has a cylindrical part 25 which lies sealingly in the ampoule unit 1 according to the invention and which has furthermore another, funnel-shaped flared end 26.

If the filling device, for example, a filling needle is now used to introduce the medium to be injected into the interior of the basic body 4, and if the injection device according to the invention is oriented vertically in the process, then any bubbles or similar air inclusions rise upward and through the filling neck 18 because of the tapered surface.

The filling neck 18 can be produced from plastic or from a metal, for example, stainless steel, and when this filling neck undergoes mechanical narrowing 27 (constriction, squeezing or the like) after the filling, the interior of the ampoule unit according to the invention is closed off completely from the outside, where a narrowing of the diameter of the filling neck at several places is definitely advantageous, to achieve a reliable absolute closure of the interior of the device according to the invention with respect to the outside.

The filling neck 18 shown in FIGS. 2a-2c remains in place after the filling, and serves during the injection process to form the piston rod which is known from the prior art, in order to press, driven by spring force, together with the applied seal 16, the medium which is located in the basic body out of the interior of the ampoule unit.

If the filling neck has several constrictions, then one constriction can also serve as a predetermined breaking point, in order to separate the filling funnel from the filling neck after filling.

Figure 3:
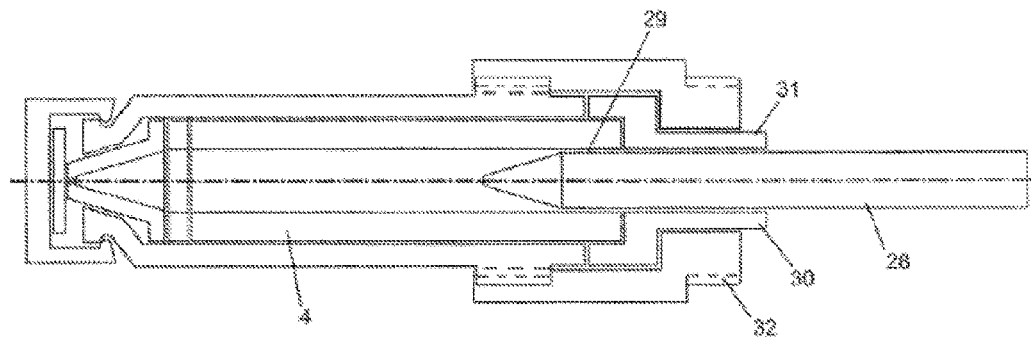
FIGS. 3-5 are cross-sectional views of injection devices.
Figure 4:
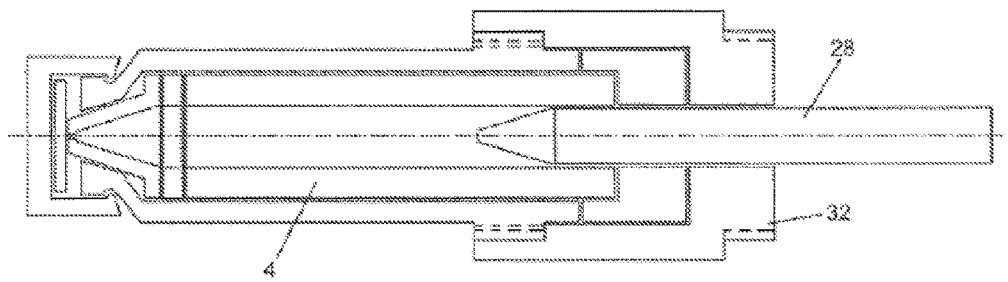

FIGS. 3 and 4 show another embodiment of the ampoule unit according to the invention in comparison with the prior art. Here one can see particularly well how, in the rear portion of the ampoule unit, a piston 28 (in the Figures, a displacement piston) is shown which is enclosed with its frontmost end inside the basic body, and in its middle area by a seal 30, where the medium which is to be pressed out of the ampoule unit according to the invention out lies like a lubricating film 29 between the piston 28 and the basic body 4 or the seal 30.

When the basic body 4 is produced here from glass (for example, boron silicate glass), then this basic body 4 can also be coated from inside with a lubricant, and thus has a streak-free, transparent appearance.

The seal 30 shown in FIG. 3 can have on the top side a ring 31 which protrudes at the top and which serves as a counter bearing applied against the piston, and, if the seal is designed to be particularly soft in this area, the abutment produced is also quite soft.

FIGS. 3 and 4 also show that the seal 30 is pressed by means of a screw-connectable cover 32 against which the shrink sleeve or the basic body can be pressed.

In FIG. 4, the cover 32 forms the upper closure, while—as already mentioned—in FIG. 3, the seal ends with a ring 31 which extends over the screw connection.

Figure 5:
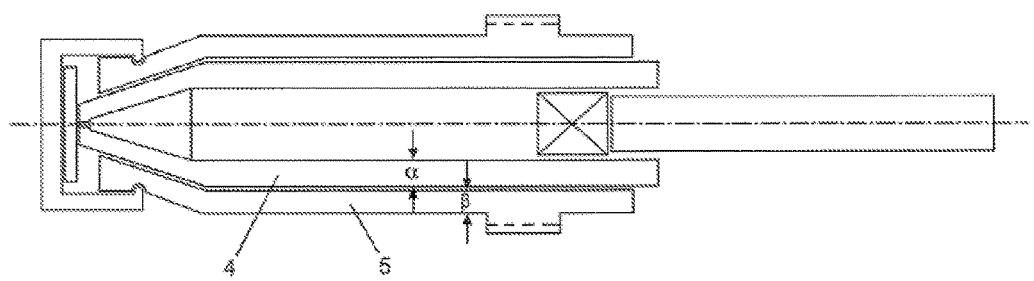

FIG. 5 shows the device according to the invention with an additional design. Here the basic body 4 is not formed, as in the prior art, from a glass material, but from a material called TOPAS. The properties and manufacture of this material are known from documents of the company TOPAS Advanced Polymers GmbH, Frankfurt or Ticon GmbH, Frankfurt (a company of Celanese AG). Not all the details are provided here on this TOPAS material. For the purposes of the present application, these mechanical, chemical and other material properties of the TOPAS material are assumed to be known, particularly in view of the fact that the material is a standard material which can be procured from various sources, particularly from the indicated procurement source. The TOPAS material is a cyclic olefin copolymer (COC), and the essential chemical, physical and other material properties of this material have been known since 2000.

Here it can be particularly advantageous for the injection device if the wall thickness α of the basic body 4 (also made of TOPAS) is smaller than the wall thickness β of the sleeve 5.

A potential additional alternative here consists in the basic body continuing to be made from a plastic or also from glass, while the inner side, however, is coated with a TOPAS material; this can be achieved, for example, by vapor deposition or by low-plasma application methods.

A particular advantage here is that the TOPAS material does not have to be depyrolyzed previously.

Figure 6:
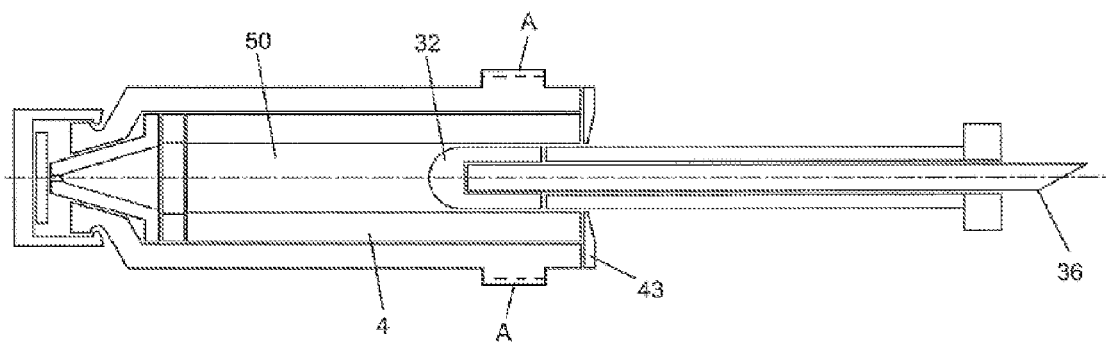
FIG. 6 is a cross-sectional view of a portion of a multi-chamber injection device.
Figure 7:
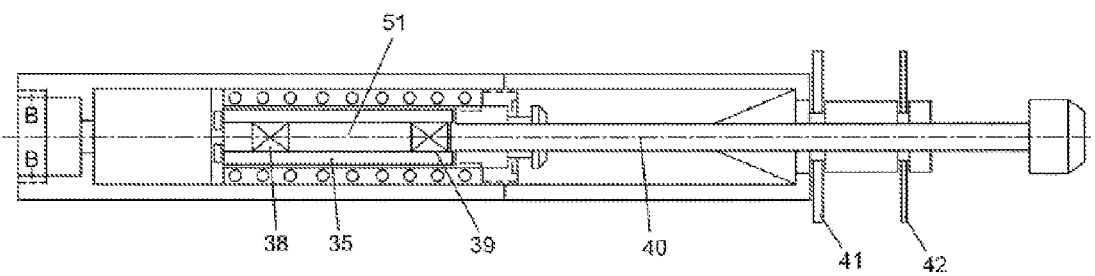
FIG. 7 is a cross-sectional view of a portion of a multi-chamber injection device.

FIGS. 6 and 7 show a variant of the known single chamber injection device which consists of a two-chamber injection device. For the purpose of representation, parts shown in FIGS. 6 and 7 are shown separately; however, they can be placed or screwed into each other, for example, particularly via the external or internal threading A-A or B-B shown in the two figures.

FIG. 6 now shows the already mentioned basic structure of the ampoule unit, where in the interior of the basic body 4, a volume is formed which is referred to as the first chamber 50 below. This first chamber is filled with a desired medium, for example, a powdery active ingredient which can be dissolved in a fluid.

FIG. 7 also shows a hollow cylindrical body 35 whose interior forms a second chamber 51.

Between the two chambers 50, 51, a connection is provided; in the represented example, the connection consists of a hollow needle 36. This hollow needle is closed at one end by a non-return valve 32 which opens into the first chamber. The other end of the hollow needle tapers (as is usually the case with a needle) to a tip (see FIG. 6), and when the two parts of the two-chamber injection device according to the invention are interconnected, the part that tapers to a tip is applied against a seal 38 which can be destroyed (or opened) by the tip of the hollow needle.

FIG. 7 also depicts the second chamber with an additional seal 39, and this seal can be pressed by a piston 40 through the cylindrical part, in order to thus press the medium which is located in the interior of the second chamber 51 through the hollow needle into the interior of the first chamber. The two media in the two chambers can be adjusted to each other in such a way that they can mix for a certain medical purpose, or also react with each other, and thus have the desired properties after mixing or after a reaction has taken place. It is here entirely possible and desirable for the two media to have a different consistency, for example, the medium in the first chamber is powdery, and the medium in the second chamber is fluid, so that, when the fluid is introduced into the powder, the powder dissolves there, and the active ingredient to be applied is formed.

At its topmost end, the injection device according to the invention according to FIGS. 6 and 7 has two safety pins 41, 42. If the first safety pin 42 is loosened, then it is possible to actuate the piston 40 manually, so that, as a result of the advance of the piston, the medium is advanced into the second chamber, so that the seal 38 which faces the tip of the hollow needle is opened or perforated, and thus the medium can move from the second chamber through the hollow needle into the interior of the first chamber.

The manual advance of the seal can here also be delimited to such an extent that the interior of the first chamber is filled with the medium from the second chamber.

If then the second safety 41 is loosened, then the entire needle-free injection device, as described in WO 2007/065544, WO 2007/065542, can be triggered, so that nearly the entire contents of the first chamber are pressed through the nozzle by the spring force.

The non-return valve 32 shown in FIG. 6 is designed as a rubber-like closure, and provided with a cut, so that when there is pressure from outside (i.e., from the interior of the 1st chamber), the valve closes, but when there is pressure from inside (i.e., from the hollow needle), the valve opens.

In FIG. 6, one can see that the basic body 4 is again completely enclosed, but on the side which is applied against the counter piece represented in FIG. 7, a flap 43 is formed which functions as a kind of small skin, or film, as a predetermined breaking point, which separates only when, after the loosening of the safety pin 41, the injection device according to the invention is triggered mechanically by the spring force.

The two chambers 50, 51 can be filled—as already mentioned—with different media, particularly media of different consistency. Thus it is particularly advantageous for the first chamber to be filled with a medium (preparation) in powdery form, for example, a lyophilisate, and the second chamber with a liquid medium, for example, a solution with isotonic NaCl (0.9%) or with a pH buffered solution, so that the powder and the fluid can be mixed together before application, or reacted extremely rapidly (less than 5 sec, preferably more rapidly than 1 sec), in order to administer certain medicinal active ingredients to a patient.

When a technical problem consists in achieving, with the injected substance, a certain administration profile under the skin of a patient, then this can be done using different measures.

Figure 8:
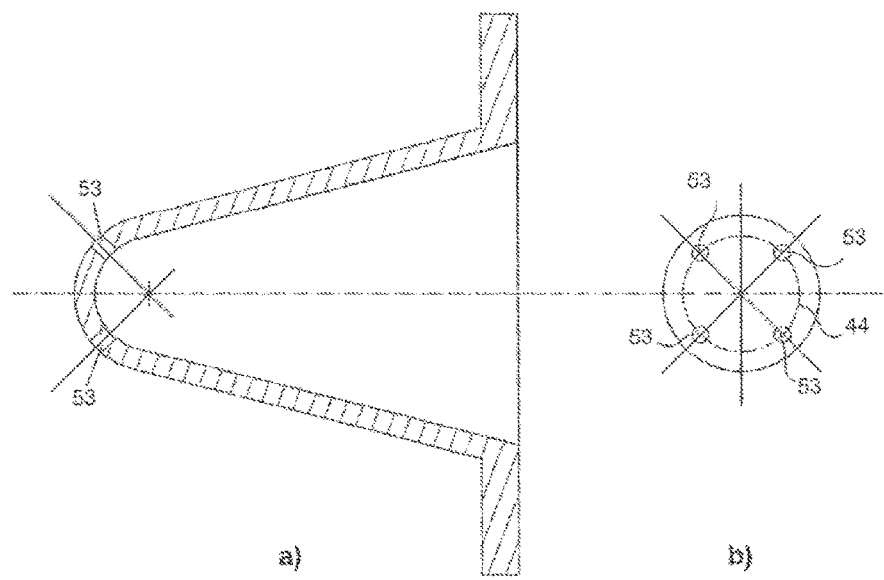

One of these measures consists in the nozzle possessing not only a single central outlet opening (as in the indicated prior art), but several outlet openings 53, and—as shown in FIG. 8 in a special example, these openings lie on an imaginary ring 44 (see FIG. 8*b*), and thus allow the medium to be administered to penetrate through the represented outlet openings at various places through the skin of the patient.

The advantage of several outlet openings is that the outlet surface area becomes overall larger, while the individual nozzles continue to be very small as before.

It is obvious that the number of outlet openings as well as their position must be designed so it is highly variable in the front nozzle area.

In the represented FIG. 8*a*, the cross section also shows that the front nozzle tip is designed as a hemisphere, which represents a very preferred embodiment. It is obvious that the size and shape of the passage surfaces of the nozzles are adapted both to the given application purpose and also to the medium, in order to achieve in this way the desired medium distribution under the skin of the patient.

Figure 9:
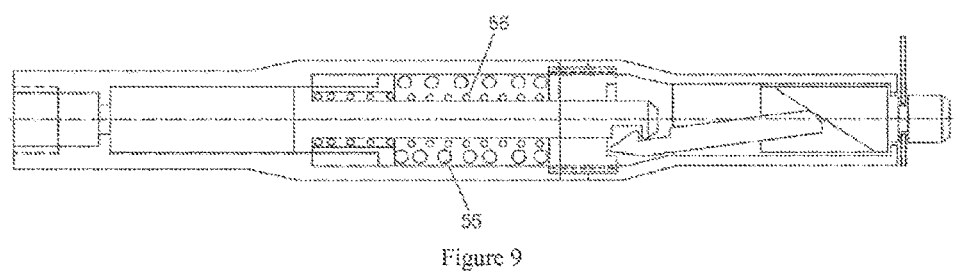
FIG. 9 is a cross-sectional view of a portion of a needle-free injection device, according to one embodiment.

FIG. 9 shows an additional embodiment of a needle-free injection device according to the invention.

Figure 10A:
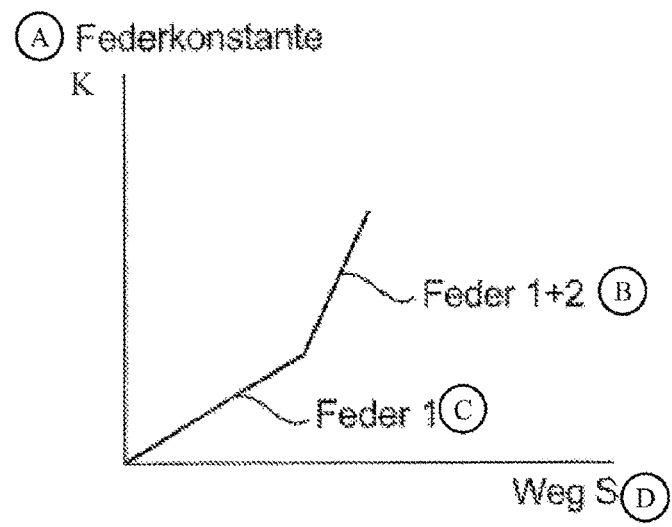
FIG. 10a is a graph showing spring characteristics.
Figure 10B:
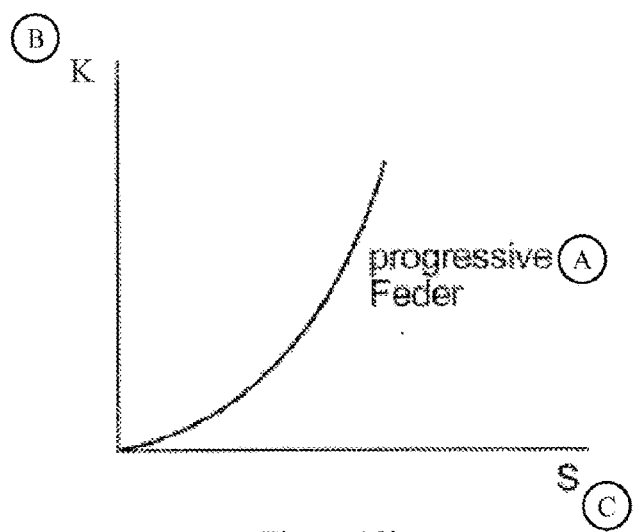
FIG. 10b is a graph showing spring characteristics.

Here one can see that not only one, single spring is designed as drive force, but immediately two springs, where the two spring 55 and 56 have different spring constants, so that the spring path characteristic curve can have a course that is not linear, as is generally the case with a spring, but a course with two different linear slopes—FIG. 10*a*—and even progressive slopes—FIG. 10*b*. FIGS. 10*a* and 10*b* provide spring path characteristic curves in which spring restoring force is plotted relative to spring deflection S to illustrate differences in the spring constants.

For example, during the advance, the strong spring at first has the prevailing effect, which can then be used to penetrate through the patient's skin, and when subsequently the second spring, which is weaker than the first spring, enters into action, the medium is then not administered deep under the skin from the injection device according to the invention, rather the injection volume is in a relatively shallow position under the skin, and the penetration depth of the injection volume can be determined by the strength of the second spring, while the first spring is importantly designed so that it first overcomes the resistance formed by the skin due to its closure.

Figure 11:
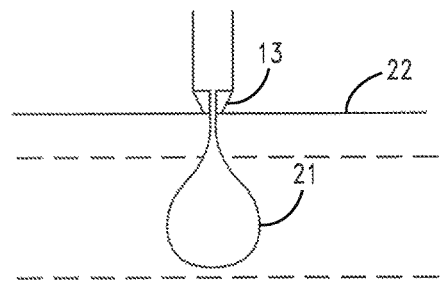
FIG. 11 shows a medium delivered into tissue.
Figure 13A:
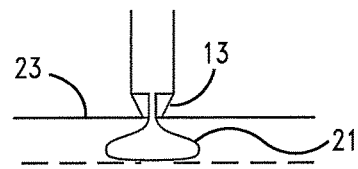
FIG. 13a shows a medium delivered into tissue.
Figure 13B:
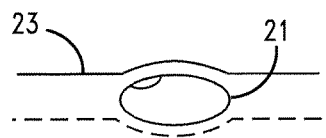
FIG. 13b shows a medium that has been delivered into tissue.

A typical spring characteristic curve of such a two-spring system is shown in FIG. 10*a*. FIG. 13 shows a possible profile of the injected medium under the skin, where one can see that this medium 21 expands relatively broadly under the skin, but does not penetrate—as shown in FIG. 11—through the skin 22 into the lower skin layers.

Figure 12:
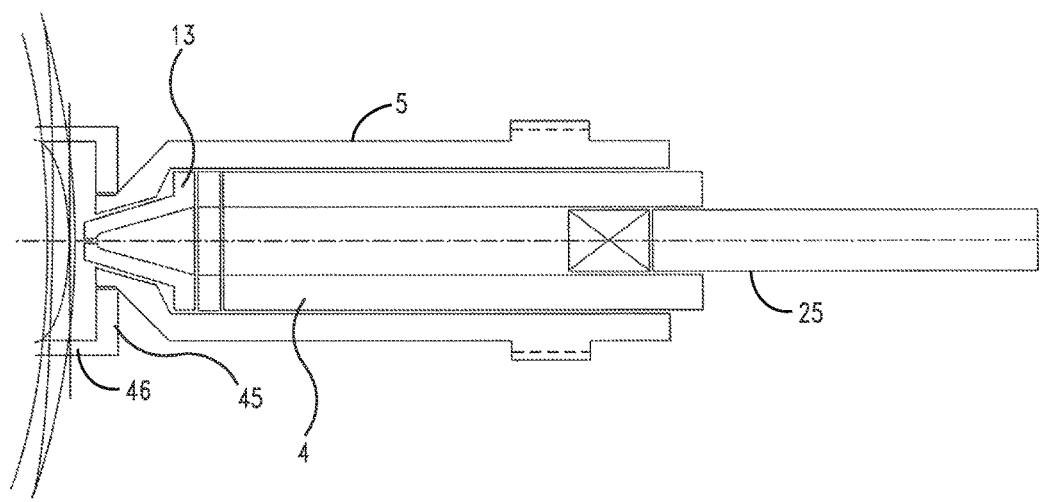
FIG. 12 shows the formation of a wheal.
Figure 12A:
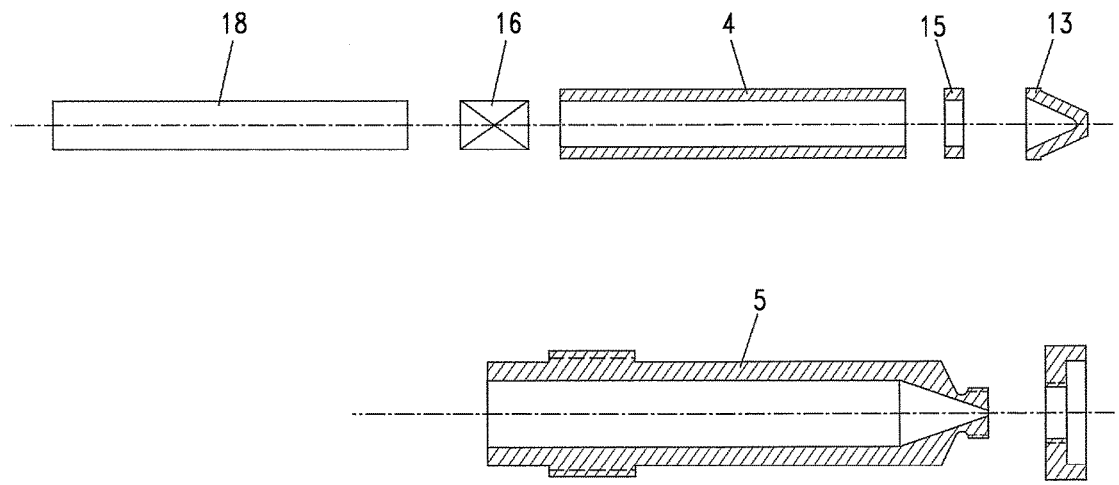
FIG. 12a is a cross-sectional, exploded view of an injection device.

FIG. 12 shows an additional—independent—design of the invention. In the solution represented in FIG. 12, the goal is mainly an optimal intradermal administration. Intradermal here means also that a visible wheal remains after the injection, the injection load is thus in a relatively shallow position in and/or under the dermis 23, and has in cross section a clearly greater surface diameter than height (see FIG. 13*a*, 13*b*).

To achieve this goal, the already described ampoule unit according to the invention is provided at its front end with an attachment 45 which is either secured firmly there or which can be attached and detached again, for example, by screw connection, etc. This extension or attachment 45 has a edge 46 which extends beyond the surface of the nozzle, for example, by approximately 0.2-0.8 mm, or by approximately 0.1-0.8 mm. In the represented example, the extension consists of a (circular) ring whose diameter substantially determines the later wheal diameter, and whose height h as represented is approximately 0.2-0.6 mm above the front nozzle surface.

The drive-out spring is also relatively weak in such a design, so that when the injection device is applied, the skin of the person who is to receive the injection bulges up in the area of the centering, and moves on the top side very close to the outlet opening of the nozzle, possibly even contacting it. As a result of this bulging, the skin is under a slight preliminary tension, and it can be pierced more easily prior to the injection, while the bulge itself also supports the wheal formation, and the spring constant of the outlet spring therefore does not need to be as strong as with an injection device where the injection must be transported into lower skin layers.

An additional variant of the invention, which is independent of the embodiment of the invention described so far, and which can also be implemented advantageously together with the previous embodiments of the invention as a single injection device, or which complements the previous embodiments of the invention, is claimed in claims 15-25 as well as in FIGS. 14*a*, 14*b* and 15*a* and 15*b*.

As already discussed, an injection device for the needle-free injection of a medium is already known from WO 2007/065542. The embodiment disclosed there is very suitable for the use of a needle-free injection of a medium.

As the embodiment represented in WO 2007/065542 shows, particularly in FIGS. 5, 6 and following, at the end facing an outlet nozzle for the medium, a triggering device is arranged, which needs only to be depressed—in a way similar to a conventional ball-point pen with a conventional pressure mechanism arranged on the back—in order to allow thus the release (activation) of the triggering device, and hence the activation of the spring drive.

As mentioned, the entire mechanism as well as the injection result is very satisfactory.

However, if a physician or possibly the patient himself/herself places the needle-free injection device with the nozzle end (i.e., the outlet end for the medium) on the skin, and wants to activate the triggering device, then psychological effects (the usual anxiety before the needle puncture) may result in the person who wants to activate the needle-free injection device, at the time when he/she wishes to release the triggering device (usually with the thumb), moving the entire injection device slightly away from the place on the body where he/she placed it earlier. At least this was observed in self-tests.

Finally, it was observed that the application pressure, i.e., the pressure with which the injection device according to WO 2007/065542 is applied on the area of the skin of the patient, is very different depending on who operates the needle-free injection device. Here too, psychological effects again play a role, but the application pressure existing before the triggering of the injection is also in each case a function of the individual himself/herself who operates the needle-free injection device. Now, it is evident that, for example when the needle-free injection device is applied with great force, the concerned area of the skin then has a very different tension than when the needle-free injection device lies merely loosely on the skin. These given different starting states, which a different skin tension, and also, under some circumstances, a different skin thickness (when the needle-free injection device is pressed on with great force, the layers under it are thus thinner than in the initial condition, without application of the needle-free injection device), so that in the end the injection of the medium can occur under very different conditions, and this accordingly also leads to different results.

To guarantee better reliability during the use of the needle free-injection device, and particularly to make the result of the needle-free injection itself more predictable and more successful, an additional design of the injection device with the characteristics of Claim 15 or 25 is described; advantageous embodiments are represented in the related dependent claims as well as in FIGS. 14 and 15.

Figure 14A:
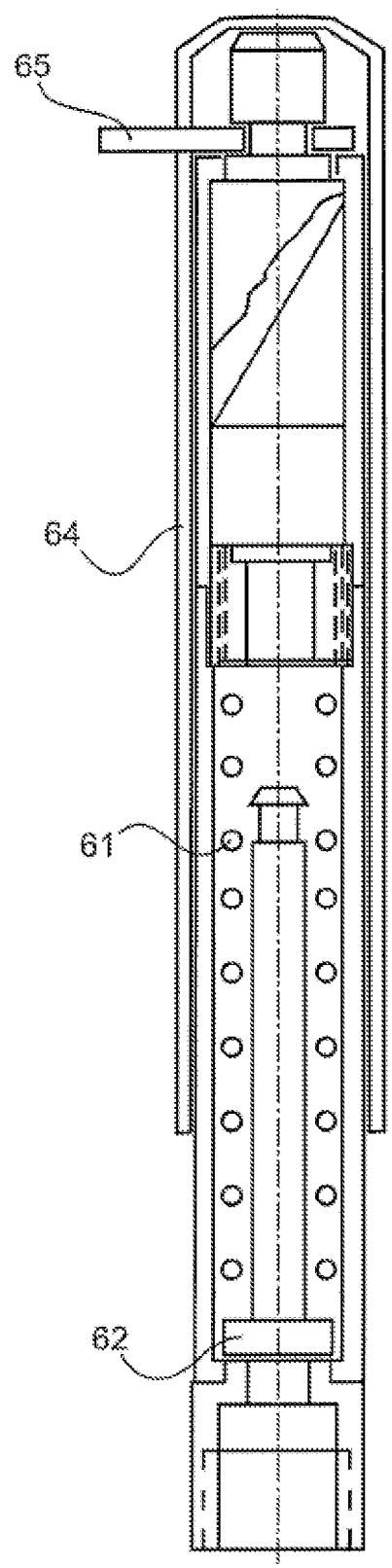
FIG. 14a is a cross-sectional view of a portion of an injection device, in accordance with one embodiment.
Figure 14B:
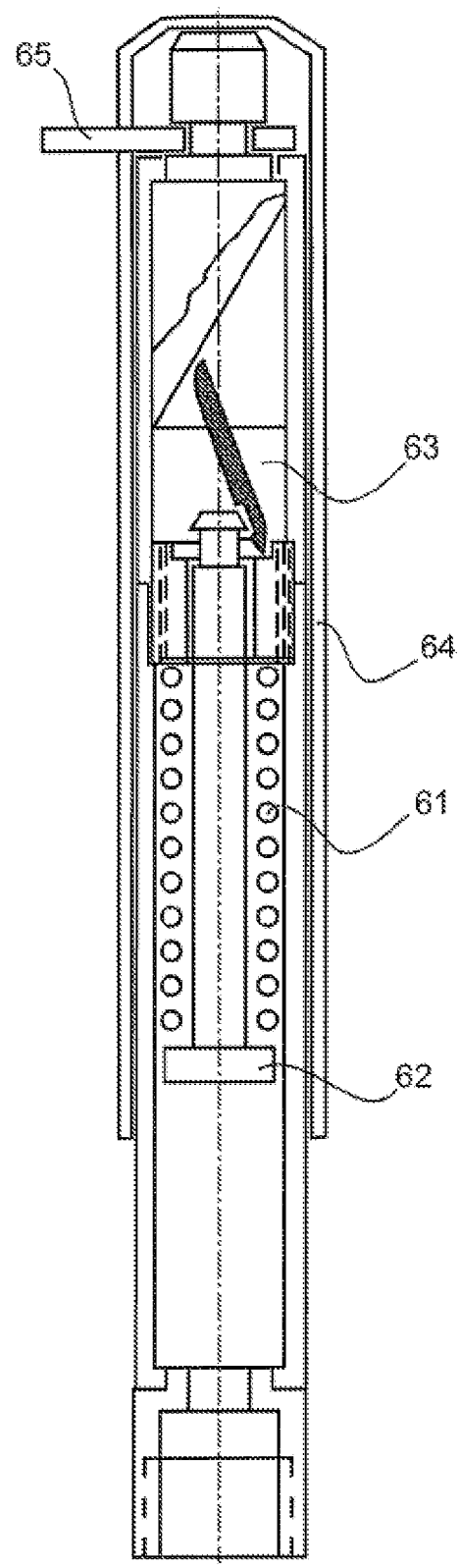
FIG. 14b is a cross-sectional view of a portion of an injection device, in accordance with one embodiment.

As one can see in FIGS. 14a and 14b, the needle-free injection device which is already known from WO 2007/065542 is provided with an enclosure, in its part that is turned away seen from the outlet end. Because the injection device in this area has a circular diameter, the enclosure also has a corresponding diameter, which, however, is slightly greater than the outer diameter of the injection device, so that encloses (in a sliding way), with its inner surface, the outer surface of the injection device in the surrounding area, while still being moveable in the longitudinal direction of the injection device. As can be seen in FIG. 14b, the enclosure also encloses the triggering element. Thus, if the enclosure is moved in the direction of the outlet end, then the triggering element is pushed simultaneously inwards, and the entire triggering of the needle-free injection is activated. As can be seen in FIGS. 14a and 14b, the enclosure may enclose at least 10% and preferably more than 40% or more than 60% of a longitudinal length of the remainder of the injection device underlying the enclosure.

To avoid unintentional triggering or shifting of the enclosure 64, an opening is provided in the top part of the enclosure, in which opening a ring-like safety element or latching element 65 is inserted, which as such is already known from WO 2007/065542. The functionality of the needle-free injection device is ensured only after this safety element or latching element 65 is pulled out of the enclosure 64.

The user can now grip the entire needle-free injection needle merely by holding on to the enclosure or its surface, and placing the injection device with its outlet end on the given skin area (substrate) where the injection is to take place. Now the user of the needle-free injection needle only needs to push the enclosure—naturally after removing the safety element—in the direction towards the area of the skin, and thus the needle-free injection always occurs under the same conditions, which means always with the same application pressure of the injection device on the given skin area. This ensures that whenever the needle-free injection needle according to the invention is triggered, the desired injection result is also always achieved reliably, and since for the entire injection only a time of approximately 10-500 msec is provided, preferably approximately 50-100 msec, then the entire injection has taken place, even if the user removes the injection device abruptly, in response to pain, for example, because the anxiety/pain reflex time is much greater than the duration of the injection itself.

Obviously the given application pressure (force) of the injection device on the skin is determined very substantially by the fact that the pressure (force) required for the triggering can also be set. The higher the pressure is that is needed to trigger the triggering element, the higher the pressure of the entire injection device on the given skin portion is as well.

As already disclosed in WO 2007/065542, the release of the driving element is achieved by swiveling or twisting a blocking device (8). This blocking device works in cooperation with the triggering element which itself is designed like a wedge. As a result of the position of the blocking device with respect to the wedge-like surface of the triggering element, on the one hand, or also by the superficial friction conditions of the blocking device, on the one hand, and the surface of the wedge-like triggering element, on the other hand, the given force (pressure) at which the triggering itself occurs can be established with great precision and particularly repeatedly, so that all injection devices of identical construction with the corresponding design are triggered at the same compressive force, and thus at the same force, with movement of the enclosure.

Naturally, it is possible to establish, by means of a different construction arrangement, different triggering forces, which under some circumstances may be desired when certain media, such as, for example, certain drugs (in liquid form) are to be administered, preferably subcutaneously, or if they are to be delivered in certain skin layers.

Figure 15A:
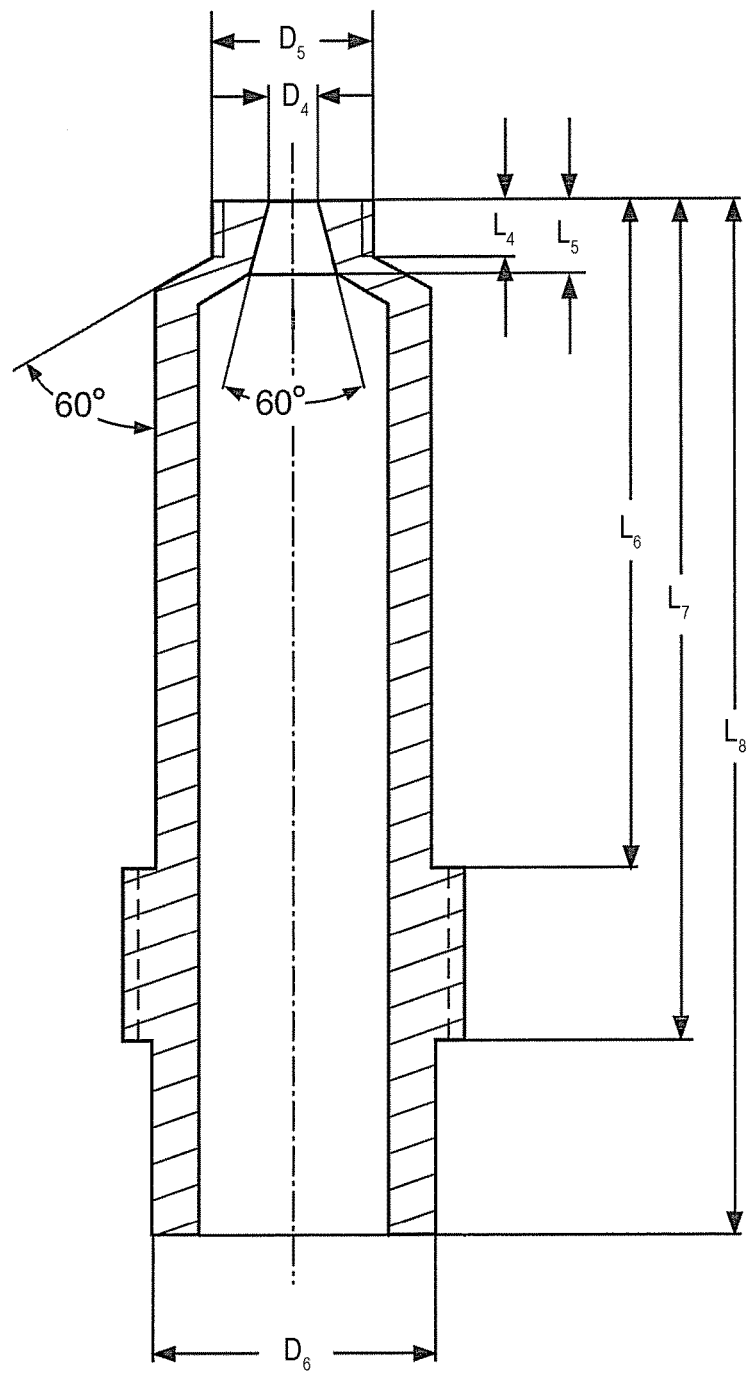
FIG. 15a is a cross-sectional view of a portion of an injection device.
Figure 15B:
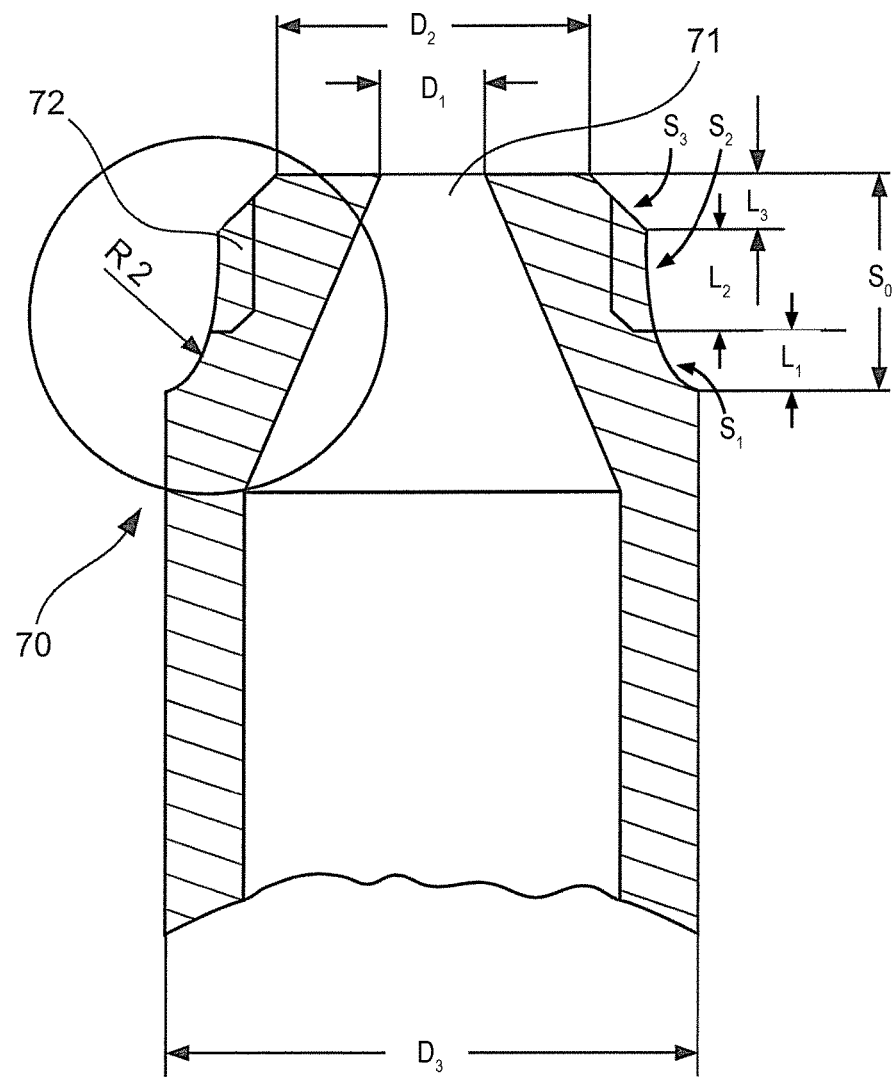
FIG. 15b is a cross-sectional view of a portion of an injection device.

An additional variant of the invention, which under some circumstances may be obvious, is indicated in FIG. 15a or 15b. This involves a modification of the variant whose principle has already been described in the provided FIG. 12.

In this variant according to FIG. 12, for the optimal intradermal administration of the injection, an attachment is placed on the nozzle end of the ampoule unit/injection device according to the invention.

FIG. 15a, and FIG. 15b now show, with greater precision, a very advantageous embodiment of the outlet end, i.e., of the end of the injection device on which the nozzle unit is formed. As one can see in FIG. 15b, the nozzle is enclosed by an enclosure or a sleeve 70, particularly a shrink sleeve, which has in a front area a first section $S_1$ in which the outer diameter of the sleeve 70 narrows—specifically as shown—in such a way that a circular arc cross section R2 (or a deviation therefrom) forms. This section $S_1$ is followed by an additional section $S_2$ in which the external threading 72 is formed (preferably a M8×1 threading) to which the attachment can be screwed. Finally, a third section $S_3$ follows in which the front end of the sleeve narrows again linearly, i.e., conically.

The first section $S_1$ has a length $L_1$ that is preferably approximately 1 mm long, and it starts at a separation $S_0$ of 4 mm seen from the nozzle end.

The second section $S_2$ has a length $L_2$ that is preferably 2 mm long, and the third section $S_3$ has a length $L_3$ that which follows the second section is approximately 1 mm long.

While the nozzle in the outlet area 71 has a diameter $D_1$ of approximately 2 mm (the nozzle opening itself has a diameter of only 0.01-0.02 mm), the diameter $D_2$ of the third section $S_3$ in the outlet area is approximately 6 mm. An outer diameter $D_3$ of the sleeve may be 10 mm.

FIG. 15a shows an enclosure according to one embodiment having the following representative dimensions: $L_4=2$ mm; $L_5=2.5$ mm; $L_6=25$ mm; $L_7=30$ mm; $L_8=37$ mm; $D_4=2$ mm; $D_5=6$ mm; and $D_6=10$ mm.

The material of the shrink material is preferably plastic, here particularly preferably polycarbonate.

The embodiment represented in FIG. 15b has the special advantage that it allows the very reliable prevention of a bursting of the ampoule during the injection, i.e., when a particularly high pressure exists in the interior of the ampoule; in particular, the embodiment disclosed in FIG. 15b can reduce the notch stresses, so that the overall material reliability is improved.

Figure 16:
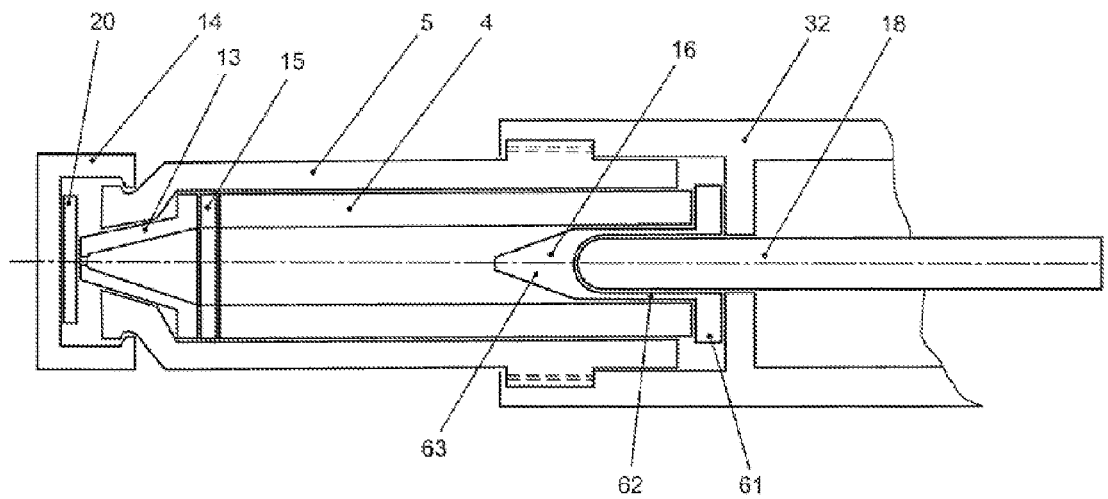
FIG. 16 is a cross-sectional view of a portion of an injection device, in accordance with one embodiment.
Figure 17:
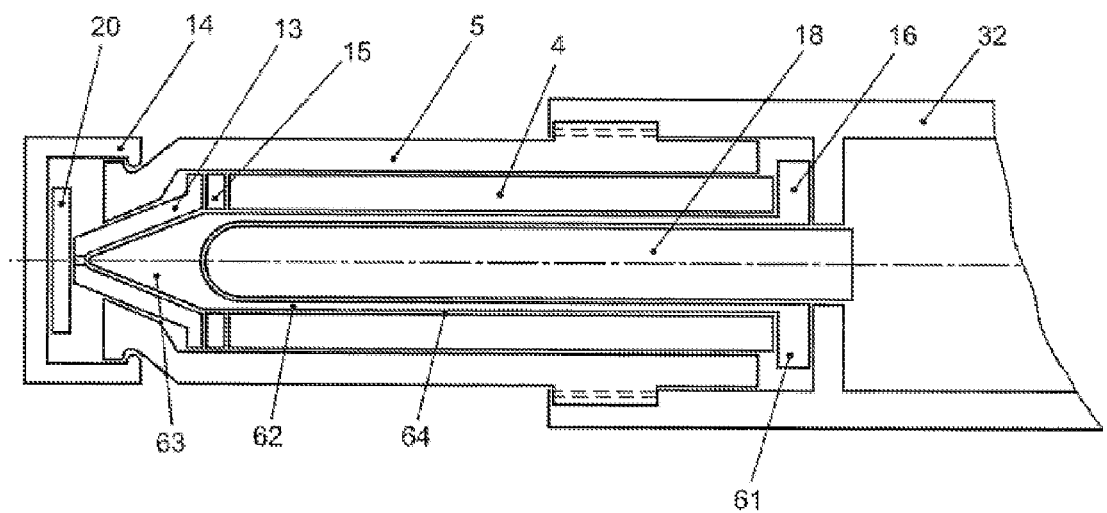
FIG. 17 is a cross-sectional view of a portion of an injection device, in accordance with one embodiment.

An additional variant of the invention, which may be independent of the embodiments and variants of the invention that have been described so far, may however also form, but which can form, together with the previous embodiments and variants, an advantageous embodiment of the invention, is described in FIGS. 16, 17 and 18.

In conventional seals of a displacement piston, overflow can occur during the use of ampoules due to high pulsating pressures. The mentioned pressures can occur, for example, in the ampoule when the displacement piston is introduced. A displacement piston can be introduced, for example via a ring seal, into the ampoule. If a sufficiently high pressure in the ampoule is then reached, then the medium located in the ampoule can escape at the contact surface between the ring seal and the piston. This can have the result of a decrease in pressure in the ampoule, which in turn may lead to failure to reach a certain pressure, which is required to inject the medium under the skin without a needle, in a problem free and reliable way, at the desired depth.

Thus, one problem of the invention is to indicate an injection device which increases the reliability of the injection. In particular, the goal is to prevent a pressure drop due to the occurrence of overflow or leaks at the introduction of a displacement piston.

FIG. 16 shows a solution according to the invention for this problem. A piston rod 18 is located in a clamped hose seal 16 which has a seal flange 61, an expandable hose 62, and a tip 63. The tip 63 is preferably designed so that it fits with positive locking in the interior part of a nozzle 13, and thus as complete as possible a displacement of a medium which is located in the interior of a basic body 4 is achieved. In principle, other designs of the tip 63 can also be used, for example, a rounded tip or a tip which is formed by the closure of the expandable hose 62, where the closure is designed such that the piston rod cannot come in contact with a medium which can be located in the interior of the basic body 4.

The nozzle 13 is closed with a cap 14 which has a cap seal 20 on the interior side. A shrink sleeve 5 encloses the basic body 4, a sealing element 15, and the nozzle 13. The shrink sleeve 5 is connectable, for example, via a nozzle connection to a cover or an injector 32.

This arrangement prevents a leak from being able to form between the piston 18 and the hose seal 16, as could occur, for example, with a ring seal. The only place in the arrangement according to FIG. 16 where a leak can occur is at the seal flange 61. However, at this place, the seal flange 61 is pressed through the screwable cover or injector 32 against the basic body 4, so that the seal is a static seal which can prevent a leak, even at high pressures in the basic body.

The hose seal 16 is inserted in the basic body of the ampoule, and the piston rod 18 is received by the expandable hose 62. As soon as the piston rod 18 moves in the direction of the nozzle 13, caused, for example, by a spring force, the expandable hose 16 is stretched, and a medium which is located inside the basic body is pressed out of the nozzle. At least a part of the piston 18 which is located inside the basic body 4 is enclosed completely by the hose seal 16. In this way one rules out the possibility of a medium which is located inside the basic body 4 coming in contact with the piston.

FIG. 17 shows the arrangement according to FIG. 16, where the piston rod 18 is now introduced entirely, i.e., up to the abutment, into the basic body 4. At the introduction of the piston rod 18, the expandable hose 16 is stretched, and in the process the wall thickness of the expandable hose 16 becomes smaller. As a result, a lubricating film 64 can form between the clamped hose seal 16 and the basic body 4.

Figure 18A:
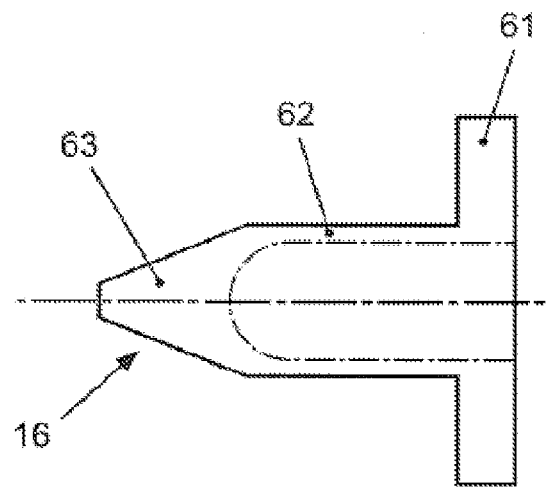
FIG. 18a is an elevational view of a hose seal.
Figure 18B:
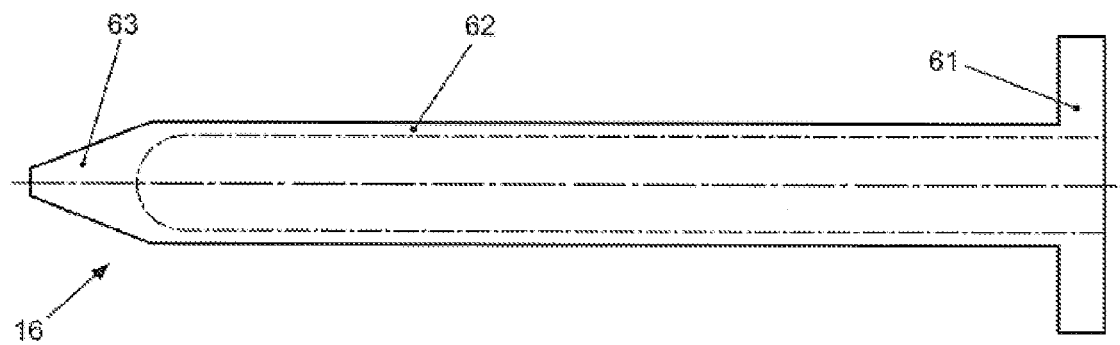
FIG. 18b is an elevational view of the hose seal of FIG. 18a in an expanded state.

FIG. 18a shows the hose seal 16, which has the seal flange 61, the tip 63, and the expandable hose 62. The hose seal is here in the non-expanded state. FIG. 18b shows the hose seal 16 according to FIG. 18a in an expanded state.

The hose seal 16 serves to receive the piston 18 and to seal the piston inlet on the basic body 4, particularly at the introduction of the piston 18. The tip 63 is preferably designed such that it can adapt with positive locking to the interior of the nozzle 13, and thus a complete displacement can be achieved. The expandable hose 62 serves to receive the movable piston 18, and to form a lubricating film 64. The seal flange 61 can be pressed against the piston input of the basic body 4, and thus serves to seal the piston inlet of the basic body 4. The lubricating film allows the sliding of the piston 18 or of the expandable hose 62 which encloses the piston 18 along an interior side of the basic body 4.

The variant represented in FIGS. 16, 17 and 18 can lead to a reliable injection. A pressure drop due to leaks and the associated loss of injection quality can thus be prevented.

The invention claimed is:

1. An injection device for the needle-free injection of a medium, the injection device comprising:
    a basic body holding the medium to be injected;
    a driving member;
    a driving element for driving the driving member to expel the medium from the basic body and for injecting the medium;
    a triggering device associated with the driving element to enable expulsion of the medium;
    a nozzle having a nozzle outlet opening through which the medium is expelled during an intradermal injection;
    an enclosure enclosing at least a portion of the injection device;
    a sleeve which encloses the nozzle, and wherein the sleeve has a first section which narrows towards an outlet thereof and is followed in a direction of the outlet by a second section, in which an outer threading is formed, and the second section is followed in the direction of the outlet by a third section in which the outer diameter of the sleeve is narrowed; and
    a nozzle attachment through which the medium flows to intradermally inject the medium, the nozzle attachment including an outer peripheral edge that extends beyond the nozzle outlet opening of the nozzle in a direction of the longitudinal axis of the injection device and parallel to the nozzle outlet opening, the outer peripheral edge being centered about the nozzle outlet opening of the nozzle and spacing the nozzle outlet opening from a surface of an injection site to assist in forming a wheal with a defined intradermal spread centered about a point of entry of the intradermal injection.

2. The injection device according to claim 1, wherein an enclosed portion of the injection device has a substantially circular cross section, and the enclosure has a substantially cylindrical shape with an inner diameter which is not substantially larger than the outer diameter of the enclosed portion of the injection device.

3. The injection device according to claim 1, wherein the enclosure comprises a plastic material.

4. The injection device according to claim 1, wherein the outer diameter narrows linearly or conically in the area of the sleeve of the first section.

5. The injection device according to claim 1, wherein the sleeve is made of a polycarbonate.

6. The injection device according to claim 1, wherein the triggering device is configured such that a pressure or a force required to activate the triggering device of the injection device corresponds to a force or a pressure exerted at the time of the injection on a substrate on which the injection device is applied during the injection.

7. The injection device according to claim 1, wherein the injection device comprises a first chamber and a second chamber, the first chamber having an interior that opens into the nozzle, the second chamber having an interior that is separated from the interior of the first chamber, wherein the interiors of the first and second chambers are connectable to each other so as to allow mixing and/or reaction of media located in the first and second chambers, and wherein a powdery medium is accommodated in the first chamber, and a fluid medium is accommodated in the second chamber, and the fluid medium is capable of being transported into the first chamber for the mixing/reaction of the two media.

8. The injection device according to claim 7, wherein the first and second chambers are connectable to each other via a hollow needle.

9. The injection device according to claim 8 wherein the hollow needle is connected by a valve to the interior of the first chamber.

10. The injection device according to claim 8, wherein the hollow needle has a needle end and a seal which closes the interior of the second chamber, the seal is capable of being destroyed so that the medium can be led into the second chamber through the interior of the hollow needle.

11. The injection device according to claim 7, wherein the injection device has a first safety element and a second safety element, wherein the first safety element is configured to prevent a connection of the inner volumes of the first and second chambers, and the second safety device is provided to prevent a triggering for pressing of the medium against the first chamber.

12. The injection device according to claim 7, wherein the first and/or the second chamber is defined by the basic body, and wherein the basic body is made from a material that has the same or similar properties as borosilicate glass.

13. The injection device of claim 1, wherein the nozzle has an outlet cross section that is round in a front part and a plurality of nozzle outlet openings.

14. The injection device according to claim 13, wherein the nozzle outlet openings lie on an imaginary circular line that extends about a longitudinal axis of the nozzle.

15. The injection device according to claim 1, wherein the nozzle attachment is detachably coupled to the injection device.

16. The injection device according to claim 15, wherein the nozzle attachment is screwed on the injection device.

17. A method of using the injection device of claim 1, the method comprising:
delivering the medium from the injection device of claim 1 to form at least one wheal with a defined intradermal spread.

18. The injection device of claim 1, wherein the injection device further comprises a spring system configured to expel out the medium from a first chamber of the basic body and the spring system has a spring characteristic curve with two or more sections forming an angle between themselves that is not equal to 180°.

19. The injection device according to claim 18, wherein the spring system of the injection device includes two springs with different spring constants.

20. The injection device of claim 1, wherein the injection device further comprises:
a hose seal for sealing a piston inlet on the basic body,
wherein the interior of the basic body serves to receive the medium, and
wherein the hose seal completely encloses at least the part of a piston which is located inside the basic body, when the piston is moved through the piston inlet into the interior of the basic body.

21. An injection device for the needle-free injection of a medium, the injection device comprising:
a basic body holding the medium to be injected;
a driving member;
a driving element for driving the driving member to expel the medium from the basic body and for injecting the medium;
a triggering device associated with the driving element to enable expulsion of the medium;
a nozzle having a nozzle outlet opening through which the medium is expelled during an intradermal injection;
an enclosure enclosing at least a portion of the injection device; and
a hose seal for sealing a piston inlet on the basic body, wherein the interior of the basic body serves to receive the medium, wherein the hose seal completely encloses at least the part of a piston which is located inside the basic body, when the piston is moved through the piston inlet into the interior of the basic body, and wherein the hose seal has a tip, an expandable hose, and a seal flange.

22. The injection device according to claim 21, further comprising: a nozzle attachment through which the medium flows to intradermally inject the medium, the nozzle attachment including an outer peripheral edge that extends beyond the nozzle outlet opening of the nozzle in a direction of the longitudinal axis of the injection device; and wherein the outer peripheral edge of the nozzle attachment is configured to contact into a subject's skin as the medium is intradermally injected into the skin so as to form a wheal that is surrounded by the outer peripheral edge of the nozzle attachment.

23. The injection device according to claim 21, further comprising: a nozzle attachment through which the medium flows to intradermally inject the medium, the nozzle attachment including an outer peripheral edge that extends beyond the nozzle outlet opening of the nozzle in a direction of the longitudinal axis of the injection device; and wherein the outer peripheral edge of the nozzle attachment is a circular ring which is aligned concentrically with the nozzle outlet opening.

24. The injection device according to claim 1, wherein the injection device includes a drive-out spring to urge the medium through the nozzle outlet opening, a strength of the drive-out spring selected such that, during the intradermal injection, the skin of a user is able to bulge toward the nozzle outlet opening in an area defined by the outer peripheral edge of the nozzle attachment.

25. The injection device according to claim 24 wherein the strength of the drive-out spring is selected such that, during the intradermal injection, the skin of the user bulges in the area defined by the outer peripheral edge of the nozzle attachment to a position near or in contact with an end surface of the nozzle.

26. The injection device according to claim 1, wherein the enclosure is configured to be shifted in a longitudinal direction of the injection device toward an end of the injection device where the nozzle outlet opening of the nozzle of the injection device is located to activate the triggering device.

27. The injection device according to claim 21, further comprising a nozzle attachment through which the medium flows to intradermally inject the medium, the nozzle attachment including an outer peripheral edge that extends beyond the nozzle outlet opening of the nozzle in a direction of the longitudinal axis of the injection device, and wherein the outer peripheral edge of the nozzle attachment extends a predefined distance beyond the nozzle outlet opening of the nozzle to define a disc-shaped cavity between the injection device and the injection site within which a the wheal is formed during use of the injection device.

28. The injection device according to claim 21, wherein the expandable hose can be expanded by the introduction of the piston, and the medium can form a lubricating film between the expandable hose and an inner wall of the basic body.

* * * * *

UNITED STATES PATENT AND TRADEMARK OFFICE
CERTIFICATE OF CORRECTION

PATENT NO. : 9,533,098 B2
APPLICATION NO. : 12/743808
DATED : January 3, 2017
INVENTOR(S) : Bernd Stormer-Talleur et al.

Page 1 of 1

It is certified that error appears in the above-identified patent and that said Letters Patent is hereby corrected as shown below:

Column 13, Line 22:
"device and the injection site within which a the wheal is"
Should read:
--device and the injection site within which a wheal is--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*